United States Patent [19]

McPhee et al.

[11] Patent Number: 5,435,315
[45] Date of Patent: Jul. 25, 1995

[54] PHYSICAL FITNESS EVALUTION SYSTEM

[76] Inventors: Ron J. McPhee, 6573 Monte Serrano NE.; Brad Sparlin, 11816 Tracey Ct. NE., both of Albuquerque, N. Mex. 87111; William Hayward, 4401 Morris NE. #214, Albuquerque, N. Mex. 87110; Samuel J. Troutman, 7113 Marilyn Ave. NE., Albuquerque, N. Mex. 87109

[21] Appl. No.: 188,249

[22] Filed: Jan. 28, 1994

[51] Int. Cl.$^6$ .............................................. A61B 05/02
[52] U.S. Cl. ...................................... 128/670; 128/668; 128/689; 128/707; 128/774
[58] Field of Search .................... 128/668, 670–672, 128/677, 689, 706, 707, 713, 716, 725, 774; 482/8, 500–502; 607/23

[56] References Cited

U.S. PATENT DOCUMENTS

| | | | |
|---|---|---|---|
| 3,675,640 | 7/1972 | Gatts | 128/671 |
| 4,281,663 | 8/1981 | Pringle | 128/707 |
| 4,367,752 | 1/1983 | Jimenez et al. | 128/707 |
| 4,566,461 | 1/1986 | Lubell et al. | 128/668 |
| 4,898,182 | 2/1990 | Hawkins et al. | 128/707 |
| 5,158,093 | 10/1992 | Shvartz et al. | 128/668 |

*Primary Examiner*—William E. Kamm
*Assistant Examiner*—Robert L. Nasser, Jr.

[57] ABSTRACT

A device for evaluating the physical fitness of an individual. The device obtains signals indicative of personal data of the individual, including cardiovascular fitness data including one of blood pressure data, heart rate data, treadmill energy expenditure data, and bicycle energy expenditure data. The device further obtains strength fitness data selected from at least one of isometric fitness data and hand strength data, flexibility fitness data, body composition data selected from at least one of weight data and percentage body fat data. The device then calculates overall fitness indices from the obtained data and outputs the indices.

19 Claims, 5 Drawing Sheets

PHYSICAL FITNESS EVALUTION SYSTEM

COPYRIGHT STATEMENT

A portion of the disclosure of this patent document contains material which is subject to copyright protection. The copyright owner has no objection to the facsimile reproduction by anyone of the patent disclosure, as it appears in the Patent and Trademark Office files or records, but otherwise reserves all copyright rights whatsoever.

FIELD OF THE INVENTION

The present invention relates to field of electro-mechanical measuring systems for evaluating physical fitness in humans and more particularly to a method and apparatus for evaluating physical fitness of individuals.

BACKGROUND OF THE INVENTION

A number of different evaluation systems are known for evaluating individual components of an individual's physical fitness, such as heart rate, blood pressure, hand strength, isometric strength, general weight, percentage body fat as determined by skin fold measurements, flexibility or range of motion, treadmill energy expenditure and bicycle energy expenditure. For example, U.S. Pat. No. 4,898,182 describes an apparatus for evaluation of heart fitness. While each such an evaluation system can measure, e.g., a particular fitness component, each component generally requires the observation and interpretation of measured parameters by an operator. Previous individual systems cannot yield an overall physical fitness evaluation.

It is an object of the present invention to provide an apparatus or system for evaluating the overall physical fitness of an individual, preferably an integrated automatic computer programmed apparatus or system for evaluating overall physical fitness indices of an individual.

It is a still further object of the invention to provide a method for readily evaluating overall physical fitness indices of an individual.

SUMMARY OF THE INVENTION

To achieve the foregoing and other objects, and in accordance with the purposes of the present invention, as embodied and broadly described herein, the present invention provides an apparatus for evaluation of physical fitness of an individual including means for obtaining personal data from said individual for classifying said individual on the basis of said data, means for measuring cardiovascular fitness of said individual, said cardiovascular fitness measurement including at least one parameter selected from the group of blood pressure measurement, heart rate measurement, treadmill energy expenditure measurement and bicycle energy expenditure measurement, means for measuring strength fitness of said individual, said strength fitness measurement including at least one parameter selected from the group of hand strength measurement and isometric strength measurement, means for measuring flexibility fitness of said individual, means for measuring body composition of said individual, said body composition measurement including at least one parameter selected from the group of weight measurement and percentage of body fat measurement, means for calculating overall physical fitness indices from the obtained individual data and the measured parameters, and, means for outputting said calculated overall physical fitness indices, wherein said apparatus is further characterized in that at least one of said measured parameters is electronically linked to said means for calculating whereby manual entry of said at least one of said measured parameters is avoided.

The present invention further provides a method of evaluating the physical fitness of an individual including obtaining individual data from said individual for classifying said individual on the basis of said data, measuring cardiovascular fitness of said individual, said cardiovascular fitness measurement including measuring at least one parameter selected from the group of blood pressure measurement, heart rate measurement, treadmill energy expenditure measurement and bicycle energy expenditure measurement, measuring strength fitness of said individual, said strength fitness measurement including measuring at least one parameter selected from the group of hand strength measurement and isometric strength measurement, measuring flexibility fitness of said individual, measuring body composition of said individual, said body composition measurement including measuring at least one parameter selected from the group of weight measurement and percentage of body fat measurement, calculating overall physical fitness indices from the obtained individual data and the measured parameters, and, outputting said calculated overall physical fitness indices, said method further characterized in that at least one of said measured parameters is electronically linked whereby said calculation is accomplished without manual entry of at least one of said measured parameters.

DETAILED DESCRIPTION

The present invention is concerned with an apparatus for the physical fitness evaluation of an individual. The present apparatus can evaluate individuals based upon comparison to national norms and is an automated system that can allow for real time evaluations. From such physical fitness evaluations, information may be provided by the apparatus relating to useful diet and exercise programs.

Figure 1:
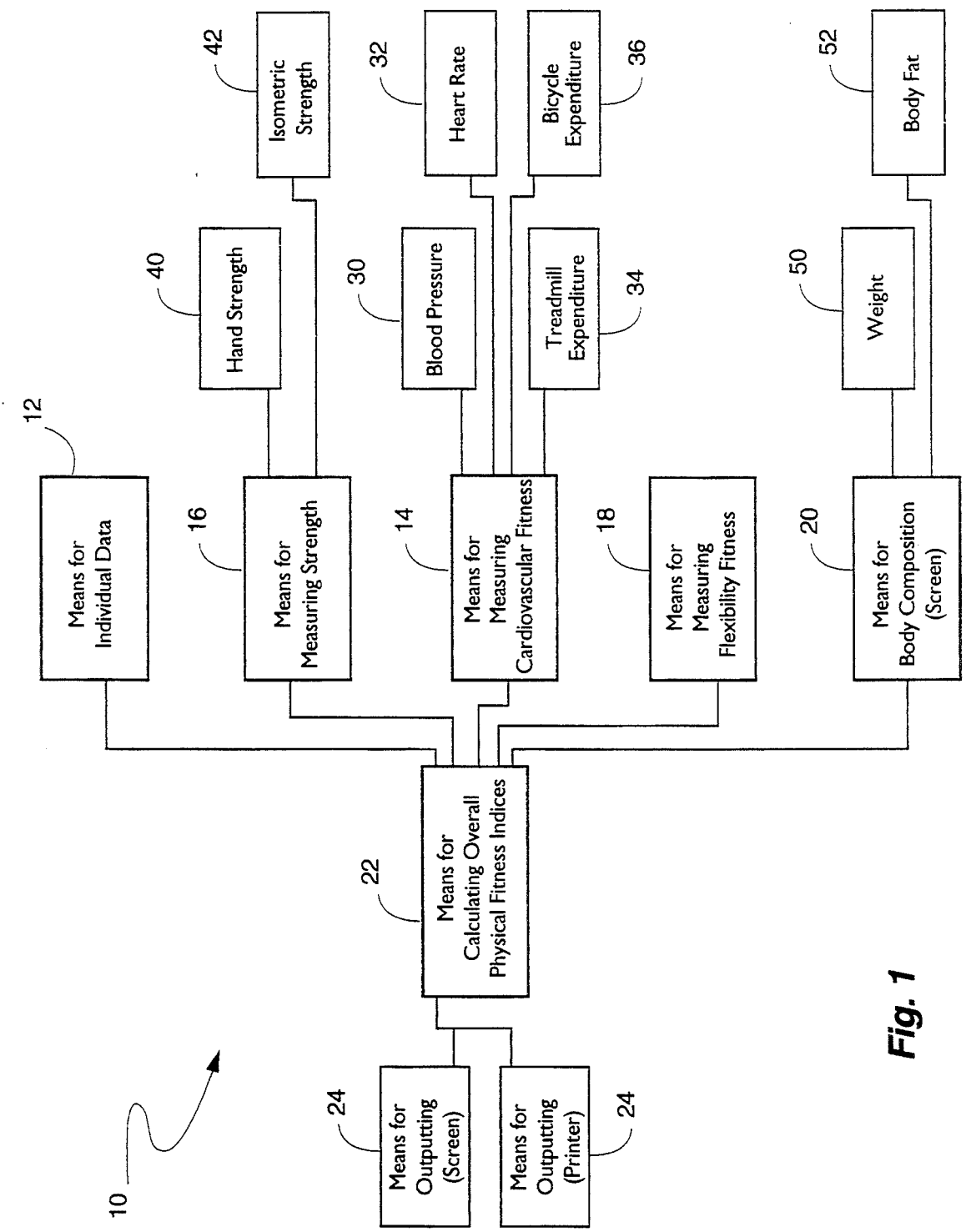
FIG. 1 illustrates a block diagram of the apparatus of the present invention.

A block diagram of the present invention is shown in FIG. 1. The physical fitness evaluation is conducted by an apparatus 10 as shown in FIG. 1 including a means 12 for obtaining individual data from said individual for classifying said individual on the basis of said data, a means 14 for measuring cardiovascular fitness of said individual, a means 16 for measuring strength fitness of said individual, a means 18 for measuring flexibility fitness of said individual, a means 20 for measuring body composition of said individual, a means for calculating overall physical fitness indices from the obtained individual data and the measured parameters, and, a means 24 for outputting said calculated overall physical fitness. In the present apparatus, a central cart can hold or contain the majority of the various sub-systems and upon the central cart can be included various shelfs or pans serving to support various parts.

The means 12 for obtaining individual data from the individual for classifying said individual on the basis of said data can include a keyboard attached to the computer. Through the keyboard an individual can input individual data such as age, sex, height, weight and any desired identifying information such as name, address and the like. Additional information such as spirometry or lung function data, blood chemistry data such as, e.g., blood cholesterol levels, high density lipoprotein levels, triglycerides levels and glucose levels, hydrostatic weighing measurements, and oxygen consumption measurements, collected externally from the present physical fitness evaluation apparatus, can also be entered. Optionally, such additional information may be entered by inclusion of additional direct electronic linkages from an additonal measurement by the present apparatus.

The means 14 for measuring cardiovascular fitness of the individual can include means for measurement of at least one parameter such as a means 30 for measuring blood pressure, a means 32 for measuring heart rate, a means 34 for measuring treadmill energy expenditure, and a means 36 for measuring bicycle energy expenditure. Generally, the more parameters within this category that are measured, the more accurate will be the overall measurement of cardiovascular fitness.

The means 30 for measuring blood pressure of the individual can be, e.g., a commercially available plug-in card, such as a Dynapulse 2000A card available from Pulse Metrics in San Diego, Calif., together with a blood pressure cuff connected to an expansion board via a pneumatic line. Resting pulse or heart beat and blood pressure is generally measured using an automated on-line or electronically linked sphygmomanometer using graphic waveforms to identify sounds and preferably approved by the American National Standards for Electronic or Automated Sphygmomanometers. When measuring the blood pressure of an individual, the individual can be seated with both feet upon the floor and the desired arm, the non-dominant arm, can be placed upon a shelf or pan of the apparatus cart at approximately heart level. The cuff can then be wrapped around the arm and blood pressure measured in a fashion common to almost anyone that has visited a doctor. The measured systolic and diastolic values will be linked through the commercial card to the computer.

Figure 2A:
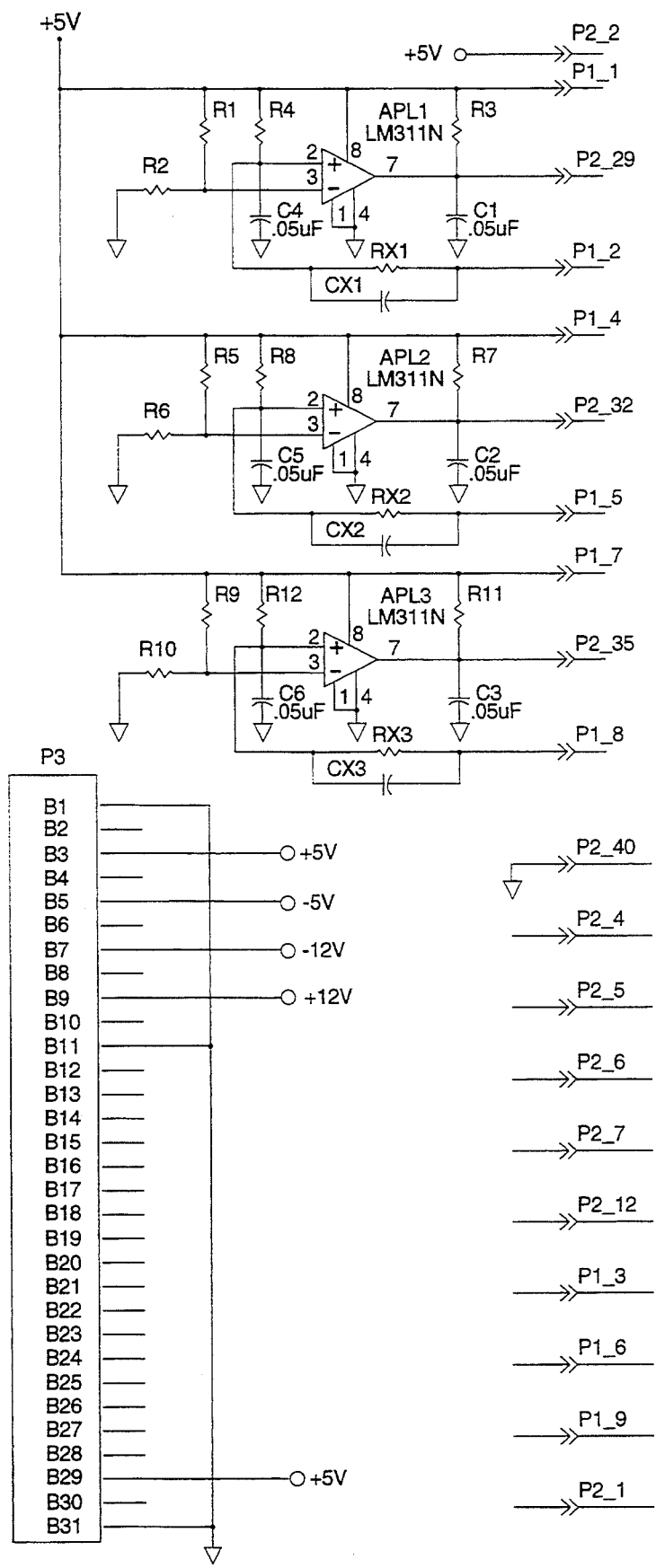
FIG. 2 is a circuit diagram of a preferred embodiment of an interface board used in the practice of the present invention.
Figure 2B:
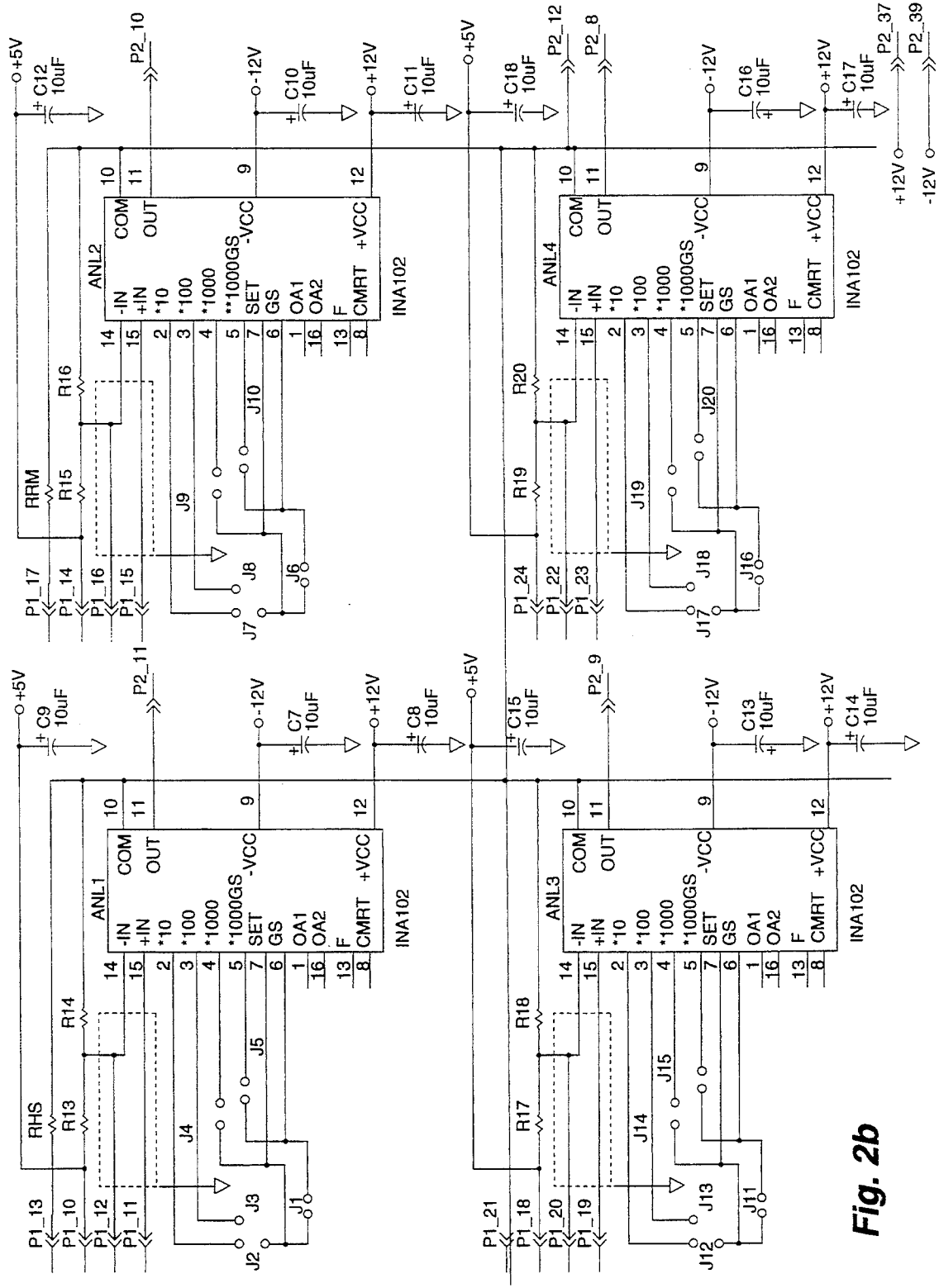

The means 32 for measuring heart rate of the individual while working can involve measurement by, e.g., a unit such as a Pulsar heart rate monitor available from Pulsar CIC in New York, preferably a wireless chest transmitter which sends an EKG signal directly to a computer via a receiver wire. In the cable to the receiver, five volts is provided from the computer to the receiver cable for operation. The received signal is passed through an interface board as shown in FIG. 2 including three pulse conditioning circuits and four analog conditioning circuits. The conditioned signal is then passed through an Analog/Digital (A/D) 210 board available from Real Time Services in State College, Pa. before passing as a digital signal to the computer.

The means 34 for measuring energy expenditure on a treadmill by the individual can involve, e.g., a treadmill such as a Trackmaster DS treadmill available from Trackmaster in Houston, Tex., with such a treadmill equipped with a RS232 port for treadmill to computer communication as a digital signal through the connector panel of the carrying cart of the apparatus. A variety of treadmill protocols are possible and include those referred to as the Modified Bruce Protocol wherein a sub-maximal test generally takes from about 6–12 minutes, the Balke Protocol wherein a sub-maximal test generally takes from about 18–20 minutes, and the Astrand Protocol wherein a sub-maximal test generally takes from about 8–14 minutes.

The means 36 for measuring energy expenditure on a bicycle by the individual can involve, e.g., a Monark 818E bike ergometer commercially available from Quintion Instruments in Seattle, Wash. Preferably, a revolutions per minute (RPM) sensor on such a bike ergometer can be modified to use switch closure of a magnet operated reed switch to generate a pulse of, e.g., 12 pulses per revolution, with the switch contacts electronically connected to the computer through an interface board as shown in FIG. 2 and an A/D 210 board to send a digital signal to the computer. Conductor cables connect from the bicycle to the connector panel of the carrying cart of the apparatus. A variety of bicycle protocols are possible and include those referred to as the Pollack Protocol wherein 3 consecutive three-minute working periods are sustained and the YMCA Protocol wherein 3–4 consecutive three-minute working periods are sustained on the bicycle.

The means 16 for measuring strength fitness of the individual can include means for measurement of at least one parameter such as a means 40 for measuring hand strength, and a means 42 for measuring isometric strength. Generally, the more parameters within this category that are measured, the more accurate will be the overall measurement of strength fitness.

The means 40 for measuring hand strength of the individual can involve measurement by, e.g., a Jamar hydraulic grip dynamometer, commercially available from Lafayette Instruments in Lafayette, Ind. The hydraulic grip dynamometer preferably includes a strain gage pressure transducer which receives necessary power from the computer. The output from the transducer which is generally at the millivolt level is then electronically linked through an interface board as shown in FIG. 2 and an A/D 210 board to the computer as a digital signal. In operation by an individual, grip size may be adjusted to a comfortable position while the individual stands erect with arms at the sides. In the overall fitness evaluation, hand strength or grip strength can generally be used as a measure of overall strength since with an average individual, hand strength or grip strength has a moderately high correlation with total strength of twenty-two other muscle groups of the body. Generally, the dynamometer can be held parallel to the individual's side with the dial facing away from the body. The dynamometer is then squeezed as hard as possible without moving the arm. Usually three repetitions are done with each hand with about a one minute rest period between repetitions. In a preferred embodiment, the hydralic grip dynamometer is connected via a retractable cable to the stand of the apparatus with the tension upon the retractable tool pulling the dynamometer snugly against the stand of the apparatus when not in use. Measured hand strength data can be compared against the grip strength norms published by Corbin et al., "Concepts in Physical Education", WCB, Dub., Iowa (1978).

The means 42 for measuring the isometric strength of the individual can include a strain gauge scale, e.g., a scale including an upper platform or plate and a lower platform or plate, plus an isometric post mounted to the lower plate of the scale. While the scale can be a single strain gauge scale, it is preferably a multiple strain gauge scale and more preferably a four strain gauge scale so that the location of an individual standing upon the upper platform or plate does not effect or negligibly effects the measured value. The isometric post is attached to an adjustable strap and handle which is used to determine isometric biceps strength when the individual pulls up on the handle whereupon a downward force results upon the upper platform including the strain gauges. The bicep strength is generally measured over the last three seconds of a five second isometric contraction in accordance with the recommended protocol of the National Institute for Occupational Safety and Health (NIOSH). The measured value is electronically linked through an interface board as shown in FIG. 2 and an A/D 210 board to the computer as a digital signal and the apparatus can then provide a comparison of the measured bicep strength with NIOSH norms and percentile rankings.

The means 18 for measuring flexibility or range of motion of the individual preferably involves a sit and reach subsystem. Such a sit and reach subsystem can include footplate and a tool balancer to retract a measuring cable and handle assembly as well as maintain tension on the cable. The cable can be constructed of, e.g., nylon, and can have a diameter of, e.g., 3/32". The handle can be of any suitable metal, preferably aluminum, and can be attached to the cable by a slot and shoulder screw. The individual, while grasping the handle attached to the cable, can sit on the floor with their back perpendicular to the floor, place their feet aginst the footplate, and gradually reach forward towards the footplate. The range of motion is determined by the cable driving a timing wheel of known diameter which in turn is attached to a ten turn variable resistor used as a voltage divider. The resultant signal is proportional to the distance traveled by the timing wheel. The signal can be electronically linked through an interface board as shown in FIG. 2 and an A/D 210 board to the computer as a digital signal. Measured values can be compared to the established norms and protocols as published by Heoger, "The Complete Guide for The Development and Implementation of Health Promotion Programs", Englewood, Colo., Morton Pub., 1987.

The means 20 for measuring body composition of the individual can include means for measurement of at least one parameter such as a means 50 for measuring weight, and a means 52 for measuring percentage of body fat. Generally, the more parameters within this category that are measured, the more accurate will be the overall measurement of body composition.

The means 50 for measuring the weight of the individual can include a platform or scale for measuring weight. Preferably, such a platform or scale includes a four load cell beam construction or four strain gauge construction overlaying a lower plate. The output of the scale is connected by a cable, e.g., a four conductor cable to a rear connector panel of the apparatus. The output signal from the scale is differential in the millivolt level thus requiring conditioning of the signal by passing through an interface board as shown in FIG. 2 and an A/D 210 board to the computer. The weight of an individual can also be manually entered without use of the scale during the collection of individual data.

The means 52 for measuring percentage of body fat of the individual can involve body fat determination using a Lange caliper. Such a caliper can be modified with a single turn variable resistor which is gear driven to provide an analog voltage proportional to the skin fold thickness measured. The signal is passed through an interface board as shown in FIG. 2 and an A/D 210 board to the computer as a digital signal. Generally, measurements can be taken by an operator at multiple sites such as chest, abdomen and thigh for men and triceps, thigh and suprailiac for women. Optionally, the means for measuring percentage of body fat can be done with a tape measure and the measurements fed manually into the computer. Such tape measurements can be taken by an operator at multiple sites such as hips, chest, abdomen and thigh for men and hips and abdomen for women. Still a further manner of determining percentage of body fat can be, e.g., by hydrostatic weighing and such a measurement can then be fed manually into the computer in place of the caliper measurements. Measured values can be compared to standard norms via the prediction equations of Jackson et al., Generalized Equations for Predicting Body Density of Men, Br. J. Nutr., vol. 40, pp. 497–504 (1978) and Jackson et al., Generalized Equations for Predicting Body Density of Women, Med. Sci. Sports Exerc., vol. 12, pp. 175–182 (1980).

The means 22 for calculating overall physical fitness indices generally involves use of a computer for determining overall physical fitness indices from the various measurements. Suitably, the computer can be an off the shelf personal computer such as an IBM or IBM-compatible computer or may be another computer such as an APPLE computer of the like. The computer is used to control data inputs, data storage, output report printing, and other functions such as graphics and operator interfaces. The computer can be modified with expansion boards to achieve the necessary functions and signal conditioning. For example, additional expansion boards can include a blood pressure board, an analog to digital converter board and an analog signal conditioning board such as shown in FIG. 2.

In FIG. 2 is shown the expansion board or analog signal conditioning board used in the present apparatus. Expansion board 100 has two types of circuits. There are three circuits configured to handle pulse type signals either as buffers or wave shaping. Thes pulse circuits, e.g., LM311 IC circuits, are single ended and require +5 Vdc to operate. This means that all pulses traverse between 0 and +5 Vdc. The remaining four circuits are analog circuits using instrument amplifiers, e.g., BB INA102 amplifiers, which are used to amplify analog signals from between 0 and +5 Vdc. These amplifiers operate from +12/−12 Vdc. The operating voltages are all obtained from the computer power supply as connected to connectors on the computer mother board.

Access to expansion board signal input connector is to the rear of the computer main frame. The expansion board is connected to the computer and the A/D 210 board using existing connectors and cables. Each remote transducer or measuring device in the apparatus is connected to the expansion board signal input connector and electronically connected to the proper pulse circuit for signal conditioning prior to outputting the conditioned signal to the A/D 210 digital conversion board whose digital signal is placed on the computer buss for processing by software.

Heart rate signals consist of a single +Vdc pulse for each heart beat. These pulses require a buffer amplifier, e.g., LM 311, APL 1 amplifier, to interface with the totalizing pulse counting circuits on the A/D 210 board. The expansion board provides the buffer which performs the sole function of impedance matching. The fixed components configured with, e.g., the APL 1 amplifier, assist in obtaining this impedance match.

Bicycle rpm signals consists of 12 +5Vdc pulses for each revolution. These pulses require a buffer amplifier, e.g., LM 311, APL 2 amplifier, to interface with the totalizing pulse counting circuits on the A/D 210 board. The expansion board provides the buffer which performs the sole function of impedance matching. The fixed components configured with, e.g., the APL 2 amplifier, assist in obtaining this impedance match. The third pulse circuit is reserved for additional future inputs.

Analog input signals require signal amplification prior to processing by the analog circuits on the A/D 210 board. These amplifying circuits use an instrument amplifier, e.g., INA102 amplifier, with amplification factors specific to the level of the input signal from the transducer or measuring device and the requirements of the analog circuits of the A/D 210 board and its conversion range of 0 to +5 Vdc.

Skinfold analog voltages are amplified by, e.g., ANL 1 amplifier, and these amplified signals are electronically connected to the analog input circuits of the A/D 210 board for digital conversion with a voltage range of 0 to 2.5 Vdc.

Hand grip analog voltages are amplified by, e.g., ANL 2 amplifier, and these amplified signals are electronically connected to the analog input circuits of the A/D 210 board for digital conversion with a voltage range of 0 to 2.5 Vdc.

Weight and isometric strength platform signals are amplified by, e.g., ANL 3 amplifier, and these amplified signals are electronically connected to the analog input circuits of the A/D 210 board for digital conversion with a voltage range of 0 to 2.5 Vdc.

Finally, range of motion or flexibility signals are amplified by, e.g., ANL 4 amplifier, and these amplified signals are electronically connected to the analog input circuits of the A/D 210 board for digital conversion with a voltage range of 0 to 2.5 Vdc.

It should be apparent that a program is needed to control the computer, to direct the operations of the computer, and to accomplish the objects of the invention during the physical fitness evaluation. The program or suitable software can be stored in the computer memory. Also stored in the computer memory will be data representing various medical data or physiologically established data of the various physical fitness parameters. For example, the bicep strength data measured by the present apparatus can be compared with NIOSH norms and percentile rankings, the flexibility data can be compared with norms and percentile rankings developed by Heoger (mentioned previously), the body composition data can be compared to the prediction equations of Jackson et al. (1978) and Jackson et al. (1980) (mentioned previously), the hand strength data can be compared with the grip strength norms of Corbin et al. (mentioned previously), and the treadmill measurement data can be compared to the protocols and norms of the Modified Bruce Protocol (mentioned previously) Other norms and protocols for comparison of the various measured data come from those of the American College of Sports Medicine, "Guidelines for Exercise Testing and Prescription" 4th Ed., Lea et al., Phil., 1991. Suitable software for receiving the various signals, calculating overall physical fitness indices and outputting the fitness result is HealthFirst System Software Plus (©), from HealthFirst Corporation, Albuquerque, N. Mex.

Figure 3:
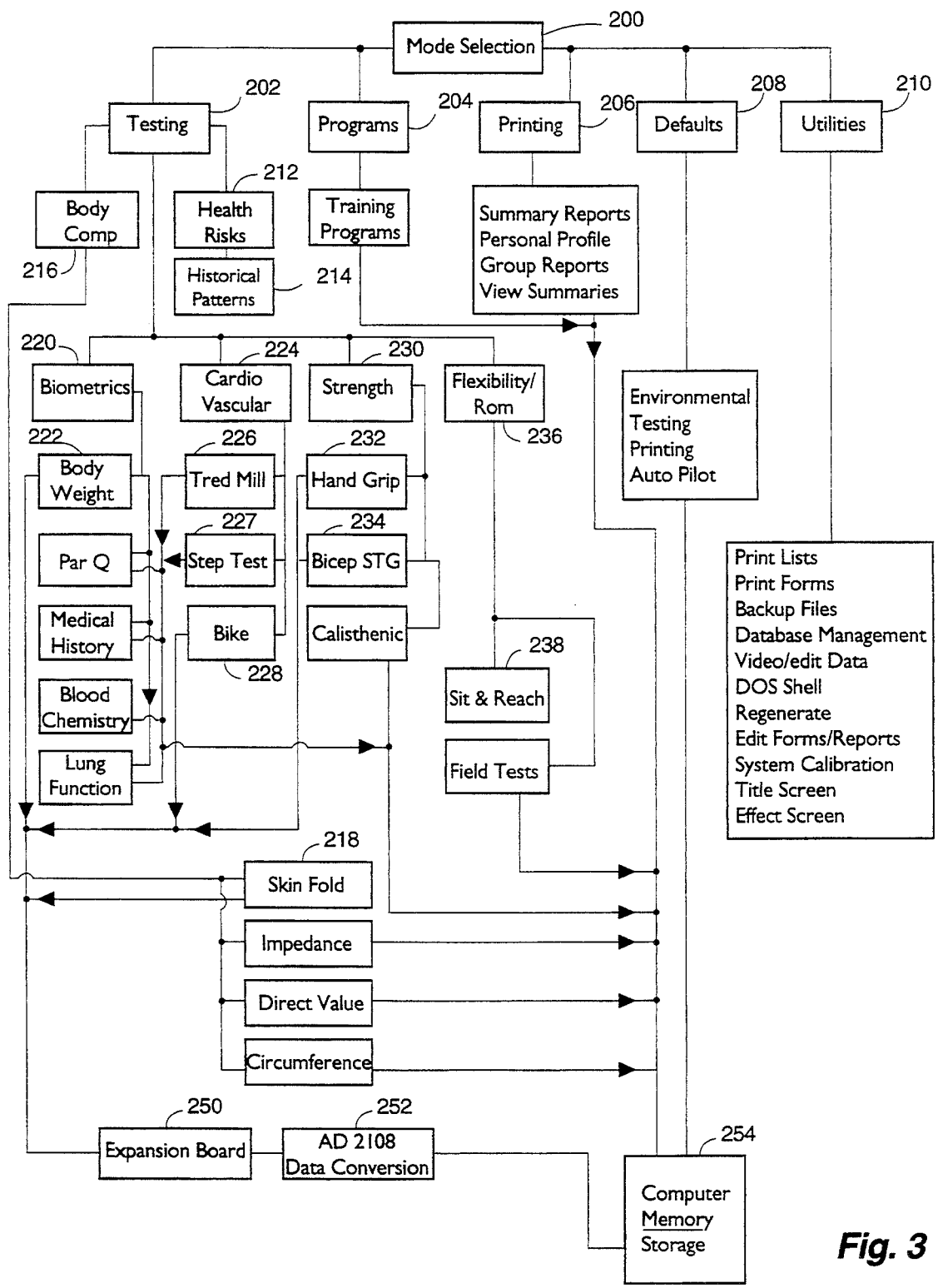
FIG. 3 is a flow diagram illustrating the functioning of a computer program or software used in the practice of the present invention.

In FIG. 3, a flow or system block diagram illustrating the functioning of the software is shown. Mode selection 200 leads to selection from among testing function 202, programs function 204, printing function 206, a defaults function 208, and a utilities function 210. From testing function 202 is evaluation of health risks at 212 to historical patterns 214. Further from testing function 202 is selection of body composition measurement 216 and control of skin fold measurement 218, selection of biometrics measurement 220 and control of weight 222, selection of cardiovascular measurement 224 and control of treadmill energy expenditure measurement 226, any step test measurement 227 and bicycle energy expenditure measurement 228, selection of stength measurement 230 and control of hand grip measurement 232 and isometric or bicep strength measurement 234, and selection of flexibility measurement 236 and control of sit and reach measurement 238. Outputs from the measurements pass through expansion board 250 and analog to digital conversion board 252 to the computer memory 254 whereat values are compared to national norms to calculate an indice of physical fitness. Additional functions of printing reports, personal profiles, any group reports and the like are selectable under printing function 206 while utilities function 210 provides for list printing, form printing, viewing and editing, DOS shell management, file management, systems calibrations, control of screens on the display screen and the like. It should be apparent that other programs could be written for control of the computer and processing of the collected data according to methods discussed elsewhere in this specification. The measured data entered into the computer memory can then be compared to various medical data or physiologically established data of the various physical fitness parameters to obtain overall indices of physical fitness.

Generally, a keyboard is attached to the computer for interfacing with the computer and a monitor is linked with the computer for display of graphics thereby serving as a visual link with an individual or operator. Means 24 of outputting the calculated physical fitness can be via a monitor screen or a printer, e.g., a Hewlett-Packard DeskJet 500 printer, attached to the computer.

Figure 4:
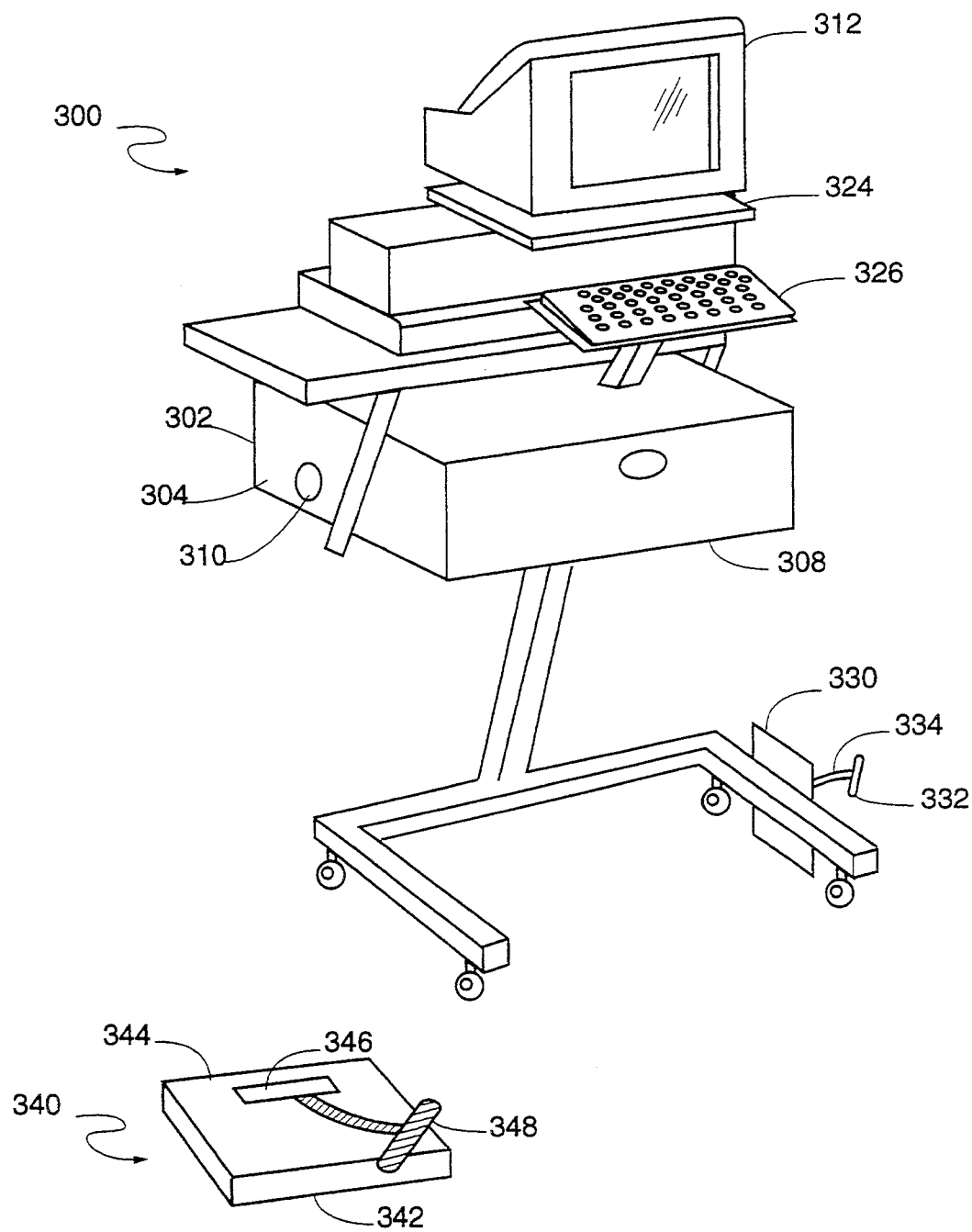
FIG. 4 is a pictorial representation of the apparatus of the present invention.

An embodiment of the present apparatus is shown in FIG. 4. Apparatus 300 includes computer 302 housed in a rear section of central housing 304. The central housing may also include a storage compartment 308 in the front section. The computer can be accessed through a removable rear panel while storage area can be accessed through a door in the front of the housing. The drive of the computer can be accessed through an opening 310 in the side of the housing. Monitor 312 is attached to computer 302 and is supported on a top pan 324 of housing 304. Keyboard 326 can be situated near the monitor on another pan of the housing. Footplate 330 is situated at one side of the central housing. Handle 332 attached to retractable cable 334 can be withdrawn by an individual to a starting position and then the handle and cable will be pulled back around the measuring wheel (not shown) as the individual reaches out towards footplate 330. Scale 340 includes the lower platform 342 and upper platform 344 including the strain gauges for measurement of weight. Addition of isometric bar 346 and adjustable strap and handle 348 allows for the isometric measurement of bicep strength when an individual pulls up on strap and handle 348.

Although the present invention has been described with reference to specific details, it is not intended that such details should be regarded as limitations upon the scope of the invention, except as and to the extent that they are included in the accompanying claims.

What is claimed is:

1. An apparatus for evaluation of the physical fitness of an individual comprising:
    means for obtaining personal data from an individual for classifying said individual on the basis of said data;
    means for receiving signals from cardiovascular fitness measurements of said individual wherein said means for receiving signals has a cardiovascular fitness output, said cardiovascular fitness measurements including at least one parameter selected from the group of blood pressure measurement, heart rate measurement, treadmill energy expenditure measurement and bicycle energy expenditure measurement;
    means for measuring strength fitness of said individual having a strength fitness output, said strength fitness measurement including at least one parameter selected from the group of hand strength measurement and isometric strength measurement;
    means for measuring flexibility fitness of said individual having a flexibility fitness output,
    means for measuring body composition of said individual having a body composition output, said body composition measurement including at least one parameter selected from the group of weight measurement and percentage of body fat measurement;
    means for calculating overall physical fitness indices from the obtained personal data, the cardiovascular fitness measurements, the strength fitness measurement, the flexibility fitness measurement and the body composition measurement by comparison with standard physical fitness values; and,
    means for outputting said calculated overall physical fitness indices, wherein, at least one of the group of cardiovascular fitness output, strength fitness output, flexibility fitness output and body composition output is electronically linked to said means for calculating whereby manual entry of said at least one of said parameters is avoided.

2. The apparatus of claim 1 wherein all of the group of cardiovascular fitness output, strength fitness output, flexibility fitness output and body composition output are electronically linked to said means for calculating whereby manual entry of said parameters is avoided.

3. The apparatus of claim 1 wherein said means for measuring flexibility is electronically linked to said calculating means.

4. The apparatus of claim 3 wherein said means for measuring strength fitness and having a strength fitness output comprises means for measuring hand strength having a hand strength output means for measuring isometric strength and having an isometric strength output, each electronically linked to said calculating means.

5. The apparatus of claim 4 wherein said means for receiving signals from cardiovascular fitness measurements comprises means for receiving an output of blood pressure and means for receiving an output of heart rate measurements, each electronically linked to said calculating means.

6. The apparatus of claim 5 wherein said means for receiving signals from cardiovascular fitness measurements further comprises means for receiving an output from energy expenditure on a treadmill by the individual and means for receiving an output from energy expenditure on a bicycle by the individual, each electronically linked to said calculating means.

7. The apparatus of claim 5 wherein said means for measuring body composition a body composition output comprises means for measuring weight having a weight output and means for measuring percentage of body fat having a body fat output, each electronically linked to said calculating means.

8. The apparatus of claim 4 wherein said means for measuring body composition a body composition output comprises means for measuring weight having a weight output and means for measuring percentage of body fat having a body fat output, each electronically linked to said calculating means.

9. The apparatus of claim 3 wherein said means for receiving signals from cardiovascular fitness measurements comprises means for receiving an output of blood pressure measurements and means for receiving an output of heart rate measurements, each electronically linked to said calculating means.

10. The apparatus of claim 9 wherein said means for receiving signals from cardiovascular fitness measurements further comprises means for receiving an output from energy expenditure on a treadmill by the individual and means for receiving an output from energy expenditure on a bicycle by the individual, each electronically linked to said calculating means.

11. The apparatus of claim 3 wherein said means for measuring body composition a body composition output comprises means for measuring weight having a weight output and means for measuring percentage of body fat having a body fat output, each electronically linked to said calculating means.

12. The apparatus of claim 1 wherein said means for measuring strength fitness comprises means for measuring hand strength and means for measuring isometric strength, each electronically linked to said calculating means.

13. The apparatus of claim 1 wherein said means for receiving signals from cardiovascular fitness measurements comprises means for receiving an output of blood pressure measurements and means for receiving an output of heart rate measurement, each electronically linked to said calculating means.

14. The apparatus of claim 13 wherein said means for receiving signals from cardiovascular fitness measurements further comprises means for receiving an output from energy expenditure on a treadmill by the individual and means for receiving an output from energy expenditure on a bicycle by the individual, each electronically linked to said calculating means.

15. The apparatus of claim 1 wherein said means for measuring body composition body composition output comprises means for measuring weight having a weight output and means for measuring percentage of body fat having a body fat output, each electronically linked to said calculating means.

16. The apparatus of claim 1 wherein the means for measuring flexibility fitness of said individual comprises a system including a footplate, a handle adapted for gripping by said individual, said handle connected to a retractable measuring cable, and a wheel having a defined diameter, said cable in contact with said wheel whereby retraction of said cable rotates said wheel in a defined fashion allowing measurement of the distance moved by said gripped handle.

17. The apparatus of claim 1 wherein the means for measuring weight of said individual and having a weight output comprises a lower plate situated upon the ground, an upper plate situated a defined distance above said lower plate by at least one spacer, and a multiple strain gauge attached to said upper plate whereby the weight of an individual upon the upper plate can be determined.

18. The apparatus of claim 17 wherein the means for measuring isometric strength comprises said lower plate, said upper plate, and said multiple strain gauge, and further includes a post attached to the lower plate and an adjustable strap and handle attached to said post whereby the isometric strength of said individual can be measured when said individual exerts an upward force upon said strap and handle.

19. A method of evaluating the physical fitness of an individual comprising:

obtaining personal data from an individual for classifying said individual on the basis of said data;

receiving signals from cardiovascular fitness measurements of said individual wherein said received signals are a cardiovascular fitness output, said cardiovascular fitness measurements including at least one parameter selected from the group of blood pressure measurement, heart rate measurement, treadmill energy expenditure measurement and bicycle energy expenditure measurement;

measuring strength fitness of said individual by measuring at least one parameter selected from the group of hand strength measurement and isometric strength measurement;

measuring flexibility fitness of said individual using a system including a footplate, a handle adapted for gripping by said individual, said handle connected to a retractable measuring cable, and a wheel having a defined diameter, whereby retraction of said cable rotates said wheel in a defined fashion allowing measurement of the distance moved by said gripping handle;

measuring body composition of said individual by measuring at least one parameter selected from the group of weight measurement and percentage of body fat measurement;

calculating overall physical fitness indices from the obtained personal data, the cardiovascular fitness measurements, the strength fitness measurement, the flexibility fitness measurement and the body composition measurement by comparison with standard physical fitness values; and, outputting said calculated overall physical fitness indices.

* * * * *